United States Patent
Snyder et al.

(10) Patent No.: US 9,234,251 B2
(45) Date of Patent: *Jan. 12, 2016

(54) BACILLUS AMYLOLIQUEFACIENS STRAIN

(75) Inventors: Amy Snyder, Salem, VA (US); Jessica Vance, Christiansburg, VA (US); Samuel Gnanmanickam, Keller, TX (US)

(73) Assignee: Novozymes Biologicals, Inc., Salem, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/051,037

(22) Filed: Mar. 18, 2011

(65) Prior Publication Data

US 2011/0230345 A1 Sep. 22, 2011

Related U.S. Application Data

(60) Provisional application No. 61/315,650, filed on Mar. 19, 2010.

(51) Int. Cl.
*C12N 1/20* (2006.01)
*A01N 59/04* (2006.01)
*A01N 63/00* (2006.01)
*C12R 1/07* (2006.01)

(52) U.S. Cl.
CPC .. *C12R 1/07* (2013.01); *A01N 63/00* (2013.01)

(58) Field of Classification Search
None
See application file for complete search history.

(56) References Cited

U.S. PATENT DOCUMENTS

| | | | |
|---|---|---|---|
| 5,171,591 A | 12/1992 | Whiting | |
| 5,242,593 A | 9/1993 | Oberkofler | |
| 5,360,517 A | 11/1994 | Guerineau | |
| 5,589,381 A | 12/1996 | Neyra | |
| 5,863,882 A | 1/1999 | Lin | |
| 6,083,718 A * | 7/2000 | Sanders et al. | 435/69.1 |
| 2008/0057670 A1 | 3/2008 | Kim | |
| 2008/0320615 A1* | 12/2008 | Johnson | 800/301 |
| 2009/0175837 A1* | 7/2009 | Yuki et al. | 424/93.46 |

FOREIGN PATENT DOCUMENTS

| | | | |
|---|---|---|---|
| AU | 719544 B2 | | 5/2000 |
| RU | 2003689 | | 3/1992 |
| WO | WO2005082149 | * | 9/2005 |
| WO | 2006/031554 A2 | | 3/2006 |
| WO | 2008/021761 A2 | | 2/2008 |

* cited by examiner

*Primary Examiner* — Blaine Lankford
*Assistant Examiner* — Lauren K Van Buren
(74) *Attorney, Agent, or Firm* — Todd Sladek

(57) ABSTRACT

The invention discloses an isolated, biologically pure culture of *Bacillus amyloliquefaciens* strain NRRL B-50349 and its use as an environmentally desirable biofungicide. The invention also discloses a formulation comprising the bacterium and a method for controlling plant fungal diseases and infestation of fungal organisms utilizing the strain.

6 Claims, No Drawings

BACILLUS AMYLOLIQUEFACIENS STRAIN

CROSS-REFERENCE TO RELATED APPLICATIONS

This application claims the benefit under 35 U.S.C. 119 of U.S. provisional application No. 61/315,650 filed Mar. 19, 2010, the contents of which are fully incorporated herein by reference.

CROSS-REFERENCE TO DEPOSITED MICROORGANISMS

The present application refers to deposited microorganisms. The contents of the deposited microorganisms are fully incorporated herein by reference.

FIELD OF THE INVENTION

The present invention relates to *Bacillus amyloliquefaciens* strain NRRL B-50349, compositions comprising the *Bacillus amyloliquefaciens* strain, and its use to control the growth of fungal and bacterial organisms, as a drain opener, and in a sanitizer formulation.

BACKGROUND OF THE INVENTION

Diseases caused by fungal species are considered among the most widespread and damaging to plants worldwide. Presently, control of plant fungal diseases is largely dependent upon the application of certain chemicals. Although some of these chemicals are known to have negative environmental and human health problems, nevertheless such chemical agents continue to be in wide use due to their strong activity against important fungal diseases, and limited availability of environmentally safer and effective alternatives.

Generally, biological control of diseases commonly infecting plants in the root zone (rhizosphere) and the leaf zone (phylloplane) are preferred over more traditional synthetic chemical control methodologies. Such biocontrol agents usually cause little or no injury to the plant host or the environment, and some may even favor normal plant development. However, most such biocontrol organisms are typically very limited either in the scope of their effectiveness against fungal diseases, or in their ability to survive under practical field conditions and during treatment applications.

Attempts have been made to control plant fungal diseases by using certain microorganisms. For example, U.S. Pat. No. 5,589,381 (Neyra and Sadasivan, 1996) describes a *Bacillus licheniformis* strain PR1-36a with some ability to inhibit certain plant pathogens. However, efforts to apply certain live biological control organisms have been greatly limited by the narrow range of their effectiveness against plant pathogens, or by the inherent instability of these organisms. Many strains often succumb within weeks to standard storage conditions, or within hours to typical field conditions involving relatively high temperatures, desiccation after spraying, and harmful effects of ultraviolet sunlight (UV) on the actively growing organism. Attempts to culture such organisms on-site at the location where the biocontrol strain would be applied have found some utility. However, serious difficulties with culture contamination, and the necessity for evening application to avoid temperature and UV effects often prove difficult, labor intensive, expensive, and impractical. Therefore, an environmentally safe and effective biological control method of inhibiting damage to plants caused by fungal diseases has heretofore not been achieved and it remains a long felt need in the agricultural industry over currently used hazardous chemicals.

TAEGRO® is a biofungicide product sold by Novozymes Biologicals Inc. for plant enhancement, growth enhancement, and suppression of certain diseases. The active ingredient is *Bacillus amyloliquefaciens* strain NZB24, which is also known as *Bacillus amyloliquefaciens* strain SB3615.

It is an object of the present invention to provide an environmentally favorable and effective biological agent for the control of a broad range of plant fungal diseases and other fungal organisms.

SUMMARY OF THE INVENTION

The present invention relates to a formulation and a biological method for controlling plant fungal diseases utilizing *Bacillus amyloliquefaciens* strain NRRL B-50349. *Bacillus amyloliquefaciens* strain NRRL B-50349 is a bacteriophage-resistant (phage-resistant) variant of *Bacillus amyloliquefaciens* strain SB3615 contained in Novozymes' product TAEGRO®. In order to propagate *Bacillus amyloliquefaciens* strain NRRL B-50349 to a number large enough to allow broad application of this strain, repeated, large-scale fermentation is required. It is known that the natural introduction of native bacteriophage (ATCC PTA-9383) can occur in standard large-scale fermentation systems over repeated growth events or batches. Such an infection can rapidly lead to a complete loss of the culture within hours or days, negating the ability to provide the strain for practical applications. *Bacillus amyloliquefaciens* strain NRRL B-50349 is resistant to such a phage (ATCC PTA-9383), and therefore maintains growth and realizes the benefits described herein.

The present invention is also directed to a liquid formulation which enhances plant growth and provides resistance to fungus or bacteria and other common plant diseases.

The present invention is also directed to a drain opener formulation comprising *Bacillus amyloliquefaciens* strain NRRL B-50349.

The present invention also relates to a sanitizing composition comprising *Bacillus amyloliquefaciens* strain NRRL B-50349 in an aqueous solution.

DETAILED DESCRIPTION OF THE INVENTION

Definitions

It should be understood that unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the methods and materials described herein are preferred. Unless mentioned otherwise, the techniques employed or contemplated herein are standard methodologies well known to one of ordinary skill in the art. The materials, methods and examples are only exemplary and not limiting.

The term "biocontrol" or "biofungicide" as used herein means controlling or eliminating the fungal or bacterial activity by biological means, such as by using a bacterium, as opposed to the use of a synthetic chemical agent.

The term "biosupplement" as used herein is defined as those naturally-occurring materials recognized to be of direct or indirect benefit to plant growth, hardiness, yield, or quality, other than commonly recognized inorganic nutrients and micronutrients. Examples of such biosupplements include: i) sea plant extracts, such as that obtained from the Norwegian kelp plant *Ascophyllum nodosum*; ii) animal manures and processed sewage sludge; iii) animal-derived products, such as bone, feather, hair, and fish meal; iv) humic and fulvic acid materials, such as from mined leornardite, peat; v) paper processing by-products (e.g., lignin sulfonate); vi) compost material obtained by microbial metabolism and partial degradation of plant and animal waste substances; and the like.

The term "propagule" as used herein refers to a component or a section of a plant containing all the essential elements to enable regrowth into a full plant and/or propagation of desired plant components. Examples of such propagules include: i) seeds; ii) eyes or "seedpieces", such as from potatoes; iii) stem cuttings which may be placed under suitable growth conditions to form new roots; iv) root or rhizome section; and the like.

Culture

The present invention is directed to a biologically pure culture of *Bacillus amyloliquefaciens* strain NRRL B-50349. In particular, the invention relates to an isolated *Bacillus amyloliquefaciens* strain NRRL B-50349, which unexpectedly possesses not only an unusually strong ability to produce potent inhibitory effect against a broad spectrum of fungal diseases, but also a natural ability to survive long-term storage and practical field application procedures or conditions.

The use of this strain provides a practical, naturally occurring alternative to standard xenobiotic chemical agents, thereby providing an environmentally safer means to achieve fungal disease control or elimination in plants.

Attributes of *Bacillus amyloliquefaciens* strain NRRL B-50349 include: efficient and rapid growth under standard large-scale fermentation conditions and media; broad temperature range for optimal growth (18-50° C.); propensity to form stable spores in a high percentage of vegetative bacterial population under known fermentation procedures; ability of the spores to survive for long periods under suboptimal conditions, such as extremes of temperature and desiccation; inherent resistance of the spores to UV sunlight; ability to grow under low oxygen conditions typically encountered in the soil and root environment; capacity to colonize the root and leaf surfaces of plants; and its verified safety to animals and plants based on standard toxicology and pathogenicity studies.

Fungicidal and Bactericidal Compositions

The present invention provides a composition comprising *Bacillus amyloliquefaciens* strain NRRL B-50349, e.g., in a form suitable for application to plants. Such a composition may comprise such common components known to one of ordinary skill in the art, as non-toxic surfactants, non-toxic amounts of plant nutrients, preservatives and the like, and may be in the form of active vegetative cells, spores, liquid, flowable powder, granules, spray dried material or with another carrier material.

A composition in accordance with the present invention is a concentrated liquid formulation which includes non-toxic amounts of plant nutrients and micronutrients, such as organic nitrogen, chelated zinc, chelated iron, as well as natural organic growth enhancing agents, such as sea plant extract. Inclusion of these ingredients, in addition to *Bacillus amyloliquefaciens* strain NRRL B-50349 in the formulation, may assist the plant in recovery from the damage and stress encountered during disease attack. Of course, as it may be suggested to those skilled in the art, other levels and types of nutrients, organic materials and the like may be substituted or added in the formulation.

The concentrate is usually diluted in about 2 to 300 volumes of water and applied by foliar spray. On turfgrass, the application rate is usually 18 ounces of the preferred formulation in 2 gallons of water sprayed on 1000 sq. ft. of turf surface using suitable liquid spray equipment. Such equipment might include application though a standard irrigation system. The amount of the preferred formulation which is applied may vary from about 2 to about 36 oz/1000 sq. ft. depending on disease pressure and overall plant health. Alternatively, a dry formulation of the invention may be prepared by spray-drying spores of *Bacillus amyloliquefaciens* strain NRRL B-50349 into a flowable powder. This may then be blended with dry nutrients, micronutrients, and organic growth agents. For application, the dry formulation containing the spray-dried spores of *Bacillus amyloliquefaciens* strain NRRL B-50349 is suspended in water to the preferred spore concentration of about $8 \times 10^7$ CFU/ml. Two gallons of this suspension are then applied on 1000 sq. ft. of plant surface, as described. The concentration of suspended spores applied per unit area may vary from about $5 \times 10^7$ CFU/sq. ft. to about $1 \times 10^{11}$ CFU/sq. ft. depending on disease pressure and type.

*Bacillus amyloliquefaciens* strain NRRL B-50349 has an unusual and surprising property of forming a dense spore coat with a high relative resistance to damage by Ultraviolet light from the sun (UV). It is also resistant to loss of viability due to desiccation and high temperature often encountered under field conditions. Furthermore, the invention provides excellent quality spores of *Bacillus amyloliquefaciens* strain NRRL B-50349 in a highly concentrated liquid form ranging from about $10^4$ to about $10^{12}$ CFU/ml. The concentrated spores could also be spray dried and used as a flowable powder with concentrations ranging from about $10^5$ to about $10^{13}$ CFU/gram or in some other suitable form.

*Bacillus amyloliquefaciens* strain NRRL B-50349 is effective against a broad array of important plant pathogenic fungi, including *Aspergillus niger*, *Bremia lactucae* (that causes Downy mildew), *Erisphe necator* (that causes Powdery mildew), *Rhizoctonia solani* (Rhizoctonia blight), *Sclerotinia sclerotiorum* (Dollar Spot disease), *Septoria apiicola*, *Spatherotheca fuligniea* (that causes Powdery mildew), *Spatherotheca macularis* (that causes Powdery mildew). *Bacillus amyloliquefaciens* strain NRRL B-50349 may also be effective against species of *Acremonium*, *Alternaria*, *Aspergillus*, *Bipolaris*, *Bremia*, *Cladosporium*, *Erisiphe*, *Microdochium*, *Pennicilium*, *Phoma*, *Pyricularia*, *Rhizoctonia*, *Sclerotinia*, *Septoria*, *Spatherotheca*, *Stachybotrys*, and *Trichophyton*, such as *Alternaria alternaria*, *Aspergillus oryzae*, *Aspergillus pullulans*, *Aspergillus versicolor*, *Bipolaris sorokiniana* (Helminthosporium blight), *Cladosporium herbarum*, *Microdochium nivale* (Pink Snow Mold), *Pyricularia grisea* (Gray Leaf Spot), *Rhizoctonia oryzae* (Rhizoctonia Sheath Spot), *Stachybotrys chartarum*, and *Trichophyton rubium*.

*Bacillus amyloliquefaciens* strain NRRL B-50349 is effective against bacterial plant pathogens such as *Erwinia*, *Pseudomonas*, *Ralstonia*, and *Xanthomonas* that cause devastating crop losses in apple, tomato and citrus. It also inhibits the growth of *Salmonella*. In particular, *Bacillus amyloliquefaciens* strain NRRL B-50349 is effective against *Erwinia amylovora* (that causes fire blight in apples, pears and prunes), *Pseudomonas syringae* pv. *phaseolicola* (that causes bacterial blight of bean), *Ralstonia solanacearum* (that causes bacterial wilt of tomato), *Salmonella choloraceus* (an enterobacter relative of *Erwinia*), and *Xanthomonas vesicatoria* (that causes bacterial spot of tomato).

Because of such demonstrated broad range efficacy and the availability of relatively large-scale growth and delivery of this unique organism, practitioners in the industry can now employ biological control methods against fungal infestation.

Methods for Controlling Fungal and Bacterial Organisms

The present invention is also directed to a method for controlling plant pathogenic fungal and bacterial species using *Bacillus amyloliquefaciens* strain NRRL B-50349 which functions by natural antagonism or growth inhibition of the disease-causing fungi and bacteria, thereby limiting the damage and spread of the harmful diseases.

The biofungicide and bacteriocide may be applied to the shoot, the leaf, the root, the seeds, vegetative propagules or as a soil or plant treatment in any suitable form, such as a liquid, a spray, a powder, root dip, a granule, a dust and the like containing active vegetative cells or spores.

Nutrient Plant Formulations

The present invention is also directed to a liquid formulation which enhances plant growth and provides resistance to fungus, bacteria and other common plant diseases. The formulation enhances plant growth in a wide variety of vegetables and ornamental plants. Thus, the formulation of the invention provides an economical and effective alternative to conventional "fertilizer" intensive growing systems.

The formulation may further comprise a blend of nutrients and micronutrients which enhance microbial activity and plant growth and health. For example, the formulation may include a phytohormone component and/or a phytohormone precursor. The *Bacillus amyloliquefaciens* strain is present in a range from about $4 \times 10^6$ to $4 \times 10^9$ CFU/ml. The formulation may also include one or more biosupplements.

Drain Opener Formulation

The present invention is also directed to a drain opener formulation, and more specifically to a formulation that provides for enhanced biological activity, safety and ease of handling.

The present invention is directed to a stable suspension of viable microorganisms, surfactant(s), and preservatives in an aqueous medium. The product has numerous advantages over currently available drain openers; such as activity at pH's closer to neutral, and solubilizing ability for soaps, fats, oils and greases. It further provides for biological activity specific to lipids, proteins and carbohydrates, and establishes a biofilm in the drains and on downstream surfaces to continuously aid the natural biodegradative process.

The composition of the present invention comprises a stable suspension of viable microorganisms, surfactant(s), preservatives, and optional fragrances in an aqueous medium with a preferred pH of approximately 5 to 6.

*Bacillus amyloliquefaciens* strain NRRL B-50349 is able to produce amylase, lipase, and protease enzymes, which catalyze the degradation of the principal chemical components of drain residues, such as grease, proteins and starches.

An operable concentration range for the microorganisms is from about $1 \times 10^6$/ml to $1 \times 10^9$/ml, with a preferred concentration being about $1 \times 10^8$, such as about $1 \times 10^7$/ml of the formulation.

Unlike typical detergents, which predominately only clean surfaces, the purpose of the surfactant in the formulation of the present invention is to solubilize grease and to make it bioavailable. This is an essential requirement of the surfactant. The surfactant can be any readily biodegradable surfactant, or a mixture of surfactants with low toxicity for the microorganisms contained within the system. The surfactant(s) must have a high grease solubilizing capability. Ionic surfactants or blends of nonionic/ionic surfactants having a hydrophile/lipophile balance approaching 10 are particularly preferred for the necessary grease solubilization. Typical surfactants suitable for use with the present invention include n-alkyl benzene sulfonates and alkyl sulfonates. Preferred nonionic surfactants include aliphatic alcohol alkoxylates, alcohol ethoxylates, polyalkylene oxide copolymers, alkyl phenol alkoxylates, carboxylic acid esters, carboxylic amides, and others. The surfactant is present in a concentration from about 3 to 10 weight percent.

The pH of the solution should be maintained as near as possible to neutral to insure adequate bacterial activity, and to minimize health risk, but be in a range compatible for surfactant activity and conducive to the survival of the bacteria. An operable pH range can be between about 3 to 10.

A preservative such as paraben, methyl paraben, or 1-2-benzisothiazolin-3-one is added to inhibit or prevent the growth of undesirable microbial contaminants in the product. The necessity for a preservative is greatest when the pH is near neutral, and the least when the pH is at the extreme ends of the operable range. The concentration of the preservative is determined by the vendor's recommendations. A typical concentration range for the preservative used in the example is from about 0.075 to 0.75 weight percent.

An additional optional preservative can be added specifically to preserve the spore form of the microorganisms. Methyl anthranilate in concentrations of from about 25 to 50 ppm (w/v) by weight has been found to be a satisfactory additive.

Optionally a chelating agent is added to enhance stabilization of the formulation.

A fragrance can optionally be added to mask the odor of the product components, and for market appeal. The fragrance must be compatible with the other components of the formulation.

Sanitizer Formulations

The present invention also relates to sanitizer formulations comprising *Bacillus amyloliquefaciens* strain NRRL B-50349. The formulations comprise a suspension of a sanitizing composition, bacterial spores, and surfactants all contained in an aqueous solution. These formulations have the advantages of being a good surface cleaning agent and a good sanitizer along with providing the long term effect of beneficial bacteria that control pathogens and degrade wastes both on the surface and in the sewage system receiving the surface rinsate.

Sanitizing agents or composition and disinfectants belong to the same category of antimicrobial (active) ingredient. Antimicrobial (active) ingredients are compounds that kill microorganisms or prevent or inhibit their growth and reproduction and that contribute to the claimed effect of the product in which it is included. More specifically, a sanitizer is an agent that reduces the number of microbial contaminants or pathogens to safe levels as judged by public health requirements.

The surfactant component functions to clean the surface by removing the soil, dirt, dried urine and soap and helps in sanitizing the surface. The sanitizing composition sanitizes the surface (kills pathogens) and preserves the formulation from contamination by unwanted microorganisms. The bacterial spores and vegetative cells function to seed the waste collection system, control odor and provide a healthy dominant microbial population that inhibits the growth of pathogens through substrate competition, production of antibiotics, etc.

In one embodiment of the present invention, the composition comprises 1,2-benzisothiazolin-3-one (Proxel), tetrasodium ethylenediaminetetraacetate (EDTA), and isopropyl alcohol (IPA) at a selected range of concentrations, combined with other components of the formula, can effectively inactivate indicator organisms. This sanitizing composition preferably is at neutral pH and does not contain chlorine-related materials, which are commonly used as sanitizers. Consequently, this sanitizing composition is more environmentally friendly and less or not corrosive.

When the formulation is applied to a bathroom fixture, sink, toilet bowl, etc., it can be sprayed or squeezed out of a container directly onto a surface or brush. The formulation is then left on the surface or scoured against the surface with a brush for not less than 10 minutes. The product is then flushed or rinsed with water and discharged from the fixture.

The formulations of the invention contain sanitizing agents, bacterial spores, and surfactants. Fragrance and dye are also added to control smell and color of the formulations, respectively. Depending on the intended use, the formulation can optionally contain an abrasive. While the key components remain the same, different thickening agents might be used in the formulation with and without an abrasive.

Although many sanitizing agents can be used for inactivating pathogens on surfaces, not all of them can be used in the present invention. This is because the sanitizing agents used in this invention are not only required to inactivate pathogens effectively, but must not have negative effects on the stability and activity of the bacterial spores contained in the formulation. In addition, the sanitizing agents are required to be relatively friendly to the environment, and should not cause skin sensitization, and should not corrode the construction materials of the fixtures on which they are used.

A unique preferred sanitizing composition which achieves the above objective is composed of Proxel, EDTA, and IPA at selected ranges of concentrations. The maximum concentration of Proxel not likely to cause skin sensitization is about 2,900 mg/L. The suitable concentration ranges of Proxel, Versene (Versene contains 39% EDTA), and IPA for producing a 4 log reduction in the count of an indicator organism in 10 minutes are 0.087 to 0.29% (vol.), 0.36 to 1.19% (vol.), and 3.5 to 7% (vol.), respectively. An additional compound, methyl anthranilate, may also be used in the formulations of the invention. The purpose of using methyl anthranilate is to assist in preservation of the formulations.

Other sanitizing agents, such as quaternary ammonium compounds (QACs), nitro-containing organosulfur and sulfur-nitrogen compounds, may also be used in the formulation of this invention.

An operable concentration range for the microorganisms is from $1\times10^5$ to $1\times10^9$ CFU/ml, such as $10^7$ CFU/ml (CFU, colony forming unit) of the formulation.

Surfactants

Surfactants are also an essential component in the sanitizer formulations of the present invention. The surfactants can wet and emulsify soil, including dirt, dried urine, soap, etc., present on a dirty surface. In addition, surfactants aid in the sanitization of the surface. Unlike surfactants usually used for surface cleaning, the surfactants used in the present invention have low toxicity for the microorganisms contained within the formulation. A single surfactant or a blend of several surfactants can be used.

Nonionic surfactants are generally preferred for use in the compositions of the present invention since they provide the desired wetting and emulsification actions and do not significantly inhibit spore stability and activity. Nonionic surfactants are surfactants having no electrical charge when dissolved or dispersed in an aqueous medium. Preferred nonionic surfactants include aliphatic alcohol alkoxylates, alcohol ethoxylates, polyalkylene oxide copolymers, alkyl phenol alkoxylates, carboxylic acid esters, carboxylic amides, and others.

Anionic surfactants or mixtures of anionic and nonionic surfactants may also be used in the formulations of the invention. Anionic surfactants are surfactants having a hydrophilic moiety in an anionic or negatively charged state in aqueous solution. Commonly available anionic surfactants include sulfonic acids, sulfuric acid esters, carboxylic acids, and salts thereof.

Abrasives, Thickening Agents, Fragrance, and Dyes

Abrasives are water-insoluble solid particles. The purpose of using abrasives is to provide deep scouring and cleaning. Depending on the application, abrasives may be optionally used in the formulation of the invention. Suitable abrasives include calcium carbonate, magnesium carbonate, silica, etc. The preferred particle size of the abrasive ranges from about 90 to 325 mesh.

Since the specific gravity of bacterial spores is usually higher than that of water, a thickening agent needs to be used in this invention to suspend the spores. Suitable aqueous thickening agents include: polyacrylic acid, polystyrene, polyvinyl alcohol, polypropylene, etc. A preferred thickening agent for suspending bacterial spores is polyacrylic acid (e.g., Acrysol TT615 from Rohm and Haas Co.). If an abrasive is used in the formulation, thickening agents in addition to polyacrylic acid might be needed to maintain the suspension of the abrasive.

A fragrance and a dye can be optionally added to mask the odor and to control the color of the product components, respectively, and for market appeal. The fragrance and dye must be compatible with the other components of the formulation.

Deposit of Biological Material

A *Bacillus amyloliquefaciens* strain was deposited under the terms of the Budapest Treaty on Apr. 12, 2010 with the Agricultural Research Service Culture Collection, 1815 North University Street, Peoria, Ill. 61604, U.S.A., under accession number NRRL B-50349. Further still, a beta-phage was deposited under the terms of the Budapest Treaty on Jul. 22, 2008 at American Type Culture Collection (ATCC), 10801 University Blvd., Manassas, Va. 20108, U.S.A., under accession number ATCC PTA-9383. The aforementioned deposits shall be maintained in viable condition at the depository during the entire term of the issued patent and shall be made available to any person or entity for use without restriction, but in accordance with the provisions of the law governing the deposits.

The following examples are given as exemplary of the invention but without intending to limit the same.

EXAMPLES

Example 1

Antifungal Assay for *Bacillus amyloliquefaciens* Strain NRRL B-50349

Bacterial cultures were prepared by picking a single colony and adding to 9 mL of plate count broth (PCB). The cultures were incubated overnight at 35° C. in a shaker. Actively growing cultures of fungi from potato dextrose agar (PDA) plates were used for the screening. These included pathogenic and nonpathogenic fungi, *Aspergillus niger*, *Rhizoctonia solani*, and *Sclerotinia sclerotiorum* (pathogen of Dollar Spot of Turf). Sterile scalpels were used to cut 5×5 mm squares of actively growing fungal mycelium. For *Rhizoctonia* and *Sclerotinia*, a mycelial bit was transferred directly to the center of a fresh PDA plate and was slightly pressed down. For *Aspergillus*, the assay was conducted by washing spores of a mycelial mat. A piece of fungus mycelium was added to 5-9 mL sterile $dH_2O$ and vortexed to obtain a dark-colored spore suspension. An aliquot of 7 micro-L of spore suspension was added as a droplet to center of PDA. Overnight-grown bacterial cultures of 3615 were diluted using PCB to adjust the cell numbers to OD of 0.2-0.4 at 600 nm. An aliquot of 7 micro-L of bacterial suspension was placed onto plates that received the fungal mycelium as droplets in three separate spots at equal spacing closer to rim of plate in two replicate plates. The plates were allowed to dry with lids off for 30 minutes. The assay plates were sealed with parafilm and incubated at 30° C. right side up. After 3-4 days, measurements of diameter of fungal inhibition zones that had developed around each bacterial spot were taken.

Three measurements of fungal inhibition were made for each of the three colonies of bacterial growth. The zones of inhibition were measured from the edge of the bacterial colony to the edge of fungal growth.

3615vpp1 demonstrated the ability to inhibit the growth of several pathogenic and non pathogenic fungi. Inhibition of *Sclerotinia sclerotiorum* DS10, causative agent of the turf disease Dollar Spot and *Rhizoctonia solani* causative agent of Brown Patch was observed with 3615vpp1. Zones of inhibition for the *Rhizoctonia* and *Sclerotinia* were 5.5 and 10.74 mm, respectively. *Aspergillus niger* was also inhibited by SB3615vPP1 which produced an 10.58 mm zone of inhibition. The data is provided in the following table:

| Strain | *Aspergillus niger* | *Rhizoctonia solani* | *Sclerotinia sclerotiorum* |
|---|---|---|---|
| 3615vPPI | 10.58 mm | 5.50 mm | 10.74 mm |
| 3615 (FZB24) | 14.22 mm | 8.85 mm | not tested |

Example 2

Phage Sensitivity Assay

*Bacillus* strain NRRL B-50349 was grown in buffered plate count broth (BPCB: 17 g m-Plate Count Broth Difco #0751-01-0 or equivalent, 20 ml of pH 7 buffer made with 1 part 9.078 g/L $KH_2PO_4$ and 1.5 parts 9.476 g/L of $K_2HPO_4$, pH adjusted to 7) to a density of approximately 0.2 absorbance units at 590 nm wavelength. 100 microliters of this culture was delivered to wells of a 96 well BD Oxygen Biosensor micro-titer plate (Catalog #353830, BD Life Sciences, San Jose, Calif.). The culture was diluted to 0.01× in additional BPCB and delivered to additional wells of the same plate. Each dilution of bacterial culture received 100 microliters of five different concentrations of phage challenge as follows: 1× (~$10^{10}$ plaque forming units/ml), 0.1×, 0.01×, 0.001×, and 0.0001×. The diluent for the phage was BPCB. One well of each bacterial culture dilution received 100 microliters of plain BPCB instead of phage and thus served as the control well. The plate was read on a BioTek Synergy kinetic plate reader at 485/20 nm excitation, 645/40 nm emission at 20 minute intervals for 20+ hours with 10 seconds of mixing at level 4 before each read. The BD Oxygen Biosensor micro-titer plates contain an oxygen sensitive fluorophore that fluoresces when the cell culture in the well consumes oxygen and thus fluorescence intensity correlates to culture growth rates and general health. Data was analyzed by comparing the fluorescent $O_2$ consumption curves of *Bacillus* strain NRRL B-50349 to curves from a separate benchmark run of *Bacillus amyloliquefaciens* strain SB3615 (growth, cell density, phage concentrations and plate contents same as described for *Bacillus* strain NRRL B-50349 above). Increasing fluorescence (bacterial growth) without decreases or plateaus (lysis or decreased growth rate) in the presence of phage was interpreted as resistance to phage. *Bacillus* strain NRRL B-50349 outperformed *Bacillus amyloliquefaciens* strain SB3615 in this way at all cell and phage densities examined. Under similar conditions, *Bacillus amyloliquefaciens* strain SB3615 succumbed to phage pressures whereas *Bacillus* strain NRRL B-50349 showed ample and prolonged proliferation despite the phage.

The present invention is described by the following numbered paragraphs:

1. A fungicidal or bacteriocidal formulation comprising *Bacillus amyloliquefaciens* strain NRRL B-50349 and a nontoxic amount of surfactant, preservative, plant nutrients, biosupplement, or a combination thereof.
2. The formulation of paragraph 1, wherein the strain is in the form of concentrated spores.
3. The formulation of paragraph 1, wherein the strain is in the form of active, vegetative cells.
4. The formulation of paragraph 2, wherein the strain is present as concentrated spores ranging from about $1 \times 10^4$ to about $1 \times 10^{12}$ CFU/ml.
5. The formulation of paragraph 2, wherein the strain is present as concentrated spores ranging from about $1 \times 10^5$ to about $1 \times 10^{13}$ CFU/g.
6. A method for controlling fungal or bacterial organisms, comprising contacting the fungal or bacterial organisms that need to be controlled, with a formulation of any of paragraphs 1-5.
7. A method for controlling fungal or bacterial organisms, comprising contacting the fungal or bacterial organisms that need to be controlled, with a fungicidal or bacteriocidal formulation comprising *Bacillus amyloliquefaciens* strain NRRL B-50349.
8. The method of paragraphs 6-7, wherein the formulation is applied as a dust, a spray, a granule, a powder or a liquid.
9. The method of paragraphs 6-7, wherein the formulation is applied as a soil treatment.
10. The method of any of paragraphs 6-9, wherein the formulation is applied to shoot, leaf, seed, vegetative propagules or root.
11. The method of any of paragraphs 6-10, wherein the fungal organisms are *Aspergillus niger, Rhizoctonia solani*, and/or *Sclerotinia sclerotiorum*.
12. The method of any of paragraphs 6-11, wherein the fungal organisms are selected from the group consisting of *Acremonium, Alternaria, Aspergillus, Bipolaris, Bremia, Cladosporium, Erisiphe, Microdochium, Pennicilium, Phoma, Pyricularia, Rhizoctonia, Sclerotinia, Septoria, Spatherotheca, Stachybotrys*, and *Trichophyton*, such as *Alternaria alternaria, Aspergillus oryzae, Aspergillus pullulans, Aspergillus versicolor, Bipolaris sorokiniana* (Helminthosporium blight), *Cladosporium herbarum, Bremia lactucae, Erisphe necator, Microdochium nivale* (Pink Snow Mold), *Pyricularia grisea* (Gray Leaf Spot), *Rhizoctonia oryzae* (Rhizoctonia Sheath Spot), *Septoria apiicola, Spatherotheca fuligniea, Spatherotheca macularis, Stachybotrys chartarum*, and *Trichophyton rubium*.
13. The method of any of paragraphs 6-12, wherein the bacterial organisms are selected from the group consisting of *Erwinia, Pseudomonas, Ralstonia, Salmonella*, and *Xanthomonas*.
14. The method of any of paragraphs 6-13, wherein the bacterial organisms are selected from the group consisting of *Erwinia amylovora, Pseudomonas syringae* pv. *Phaseolicola, Ralstonia solanacearum, Salmonella choloraceus*, and *Xanthomonas vesicatoria*.
15. A method of enhancing plant growth and providing resistance to fungus or bacteria, comprising applying to a plant *Bacillus amyloliquefaciens* strain NRRL B-50349.

16. A drain opener formulation comprising *Bacillus amyloliquefaciens* strain NRRL B-50349 and a surfactant.

17. A sanitizing composition comprising *Bacillus amyloliquefaciens* strain NRRL B-50349 and a surfactant.

18. A biologically pure culture of *Bacillus amyloliquefaciens* strain NRRL B-50349.

Example embodiments have now been described in accordance with the objects and advantages of the present invention. It will be appreciated that these examples are merely illustrative and not limiting of the invention. Many variations and modifications will be apparent to those skilled in the art and all such variations and modifications are included within the purview and scope of the claims.

What is claimed is:

1. A method for controlling fungal or bacterial organisms, comprising applying a formulation including a biologically pure culture of *Bacillus amyloliquefaciens* having the deposit accession number NRRL B-50349 and a nontoxic amount of surfactant, preservative, plant nutrients, biosupplement, or a combination thereof to soil, shoots, leaves, seeds, vegetative propagules, roots, drains, and other surfaces having bacterial and/or fungal contamination.

2. The method of claim 1, wherein the formulation is applied as a dust, a spray, a granule, a powder or a liquid.

3. The method of claim 1, wherein the fungal organisms are *Aspergillus niger*, *Rhizoctonia solani*, and/or *Sclerotinia sclerotiorum*.

4. The method of claim 1, wherein the fungal organisms are selected from the group consisting of *Acremonium*, *Alternaria*, *Aspergillus*, *Bipolaris*, *Bremia*, *Cladosporium*, *Erysiphe*, *Microdochium*, *Penicillium*, *Phoma*, *Pyricularia*, *Rhizoctonia*, *Sclerotinia*, *Septoria*, *Sphaerotheca*, *Stachybotrys*, *Trichophyton*, *Alternaria alternata*, *Aspergillus oryzae*, *Aureobasidium pullulans*, *Aspergillus versicolor*, *Bipolaris sorokiniana* (*Helminthosporium blight*), *Cladosporium herbarum*, *Bremia lactucae*, *Erysiphe necator*, *Microdochium nivale* (*Pink Snow Mold*), *Magnaporthe grisea* (*Gray Leaf Spot*), *Rhizoctonia oryzae* (*Rhizoctonia Sheath Spot*), *Septoria apiicola*, *Sphaerotheca fuliginea*, *Podosphaero macularis*, *Stachybotrys chartarum*, and *Trichophyton rubrum*.

5. The method of claim 1, wherein the bacterial organisms are selected from the group consisting of *Erwinia*, *Pseudomonas*, *Ralstonia*, *Salmonella*, and *Xanthomonas*.

6. The method of claim 1, wherein the bacterial organisms are selected from the group consisting of *Erwinia amylovora*, *Pseudomonas syringae* pv. *phaseolicola*, *Ralstonia solanacearum*, *Salmonella choleraesuis*, and *Xanthomonas vesicatoria*.

* * * * *